(12) United States Patent
Hansen

(10) Patent No.: US 6,357,438 B1
(45) Date of Patent: Mar. 19, 2002

(54) IMPLANTABLE SENSOR FOR PROPORTIONAL ASSIST VENTILATION

(75) Inventor: Gary Hansen, Eden Prairie, MN (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/691,171

(22) Filed: Oct. 19, 2000

(51) Int. Cl.[7] .......................... A61M 16/00; A62B 7/00
(52) U.S. Cl. ........................ 128/204.18; 128/204.21; 128/204.23; 607/42
(58) Field of Search ................. 128/204.18, 204.21, 128/204.23; 607/42; 600/529, 531, 532, 534, 536, 538

(56) References Cited

U.S. PATENT DOCUMENTS

| | | | | |
|---|---|---|---|---|
| 5,174,287 A | * | 12/1992 | Kallok et al. | 128/419 |
| 5,483,969 A | * | 1/1996 | Testerman et al. | 128/716 |
| 5,485,851 A | * | 1/1996 | Erickson | 128/716 |
| 5,522,862 A | * | 6/1996 | Testerman et al. | 607/42 |
| 5,540,731 A | * | 7/1996 | Testerman | 607/42 |
| 5,540,732 A | * | 7/1996 | Testerman | 607/42 |
| 5,540,733 A | * | 7/1996 | Testerman et al. | 607/42 |
| 5,549,655 A | * | 8/1996 | Erickson | 607/42 |
| 5,895,360 A | * | 4/1999 | Christopherson et al. | 600/529 |
| 5,944,680 A | * | 8/1999 | Christopherson et al. | 607/24 |
| 5,988,171 A | * | 11/1999 | Sohn et al. | 128/848 |
| 6,021,352 A | * | 2/2000 | Christopherson et al. | 607/42 |
| 6,099,479 A | * | 8/2000 | Christopherson et al. | 600/529 |
| 6,132,384 A | * | 10/2000 | Christopherson et al. | 600/529 |
| 6,289,237 B1 | * | 9/2001 | Mickle et al. | 600/509 |

* cited by examiner

Primary Examiner—John G. Weiss
Assistant Examiner—Darwin P. Erezo
(74) Attorney, Agent, or Firm—Rothwell, Figg, Ernst & Manbeck

(57) ABSTRACT

A ventilator system using an implantable respiration sensor ventilator and a method for providing a proportional respiration assist are provided according to an embodiment of the invention. The implantable respiration sensor includes a respiration sensor element capable of being implanted in a patient. The respiration sensor element generates a respiration signal related to a respiration of the patient. The implantable respiration sensor further includes a respiration signal relay device capable of being implanted in the patient and in communication with the respiration sensor element. The respiration signal relay device is capable of communicating the respiration signal to a ventilator that is external to the patient. Using the implantable respiration sensor, a predetermined gas charge may be delivered to the patient based on the respiration signal.

27 Claims, 3 Drawing Sheets

IMPLANTABLE SENSOR FOR PROPORTIONAL ASSIST VENTILATION

BACKGROUND OF THE INVENTION

1. Field of the Invention

The present invention relates generally to the field of medical ventilators.

2. Description of the Background Art

A medical ventilator is a device that aids or boosts breathing in a patient. The ventilator is generally some form of gas pump that supplies air or gas to the patient at a positive relative pressure (i.e., greater than the ambient air pressure). The ventilator may therefore aid in supplying air to a patient's lungs, even when the patient needs assistance or when the patient is unable to breathe on his or her own.

In certain types of medical conditions, such as pneumonia, for example, breathing may be laborious for the patient. This may be due to inflammation or blockage of the airways or lungs, damage to the ribs, lungs, or diaphragm muscles, etc. In such circumstances, the patient may not have sufficient stamina for prolonged struggle, or may be weakened by the effort of breathing. Ventilation of the patient may therefore be needed or required.

A prior art ventilator is a mechanical device that functions to pump air into the patient's lungs. However, it is generally a machine that provides a fixed volume for each inhalation. It does not detect or adapt to the patient's respiratory requirements. The prior art ventilator is typically constructed to operate on a fixed time cycle and provide a fixed air charge.

This is done in order to avoid overcharging the patient's lungs and causing damage to the patient's respiratory system. The prior art ventilator may be calibrated to an approximate patient capacity before operation.

The prior art ventilator therefore has drawbacks in that it generally is not responsive to the respiratory needs of the patient. The prior art ventilator does not directly measure or detect an effort of the patient in order to adjust or more fully assist the patient's breathing. The prior art ventilator therefore cannot anticipate a larger inspiration volume demand by the patient, or an inspiration of a varying duration or frequency. Most of all, however, the prior art ventilator cannot provide a varying gas charge output in order to aid the patient in cases where the patient increases his or her effort in an attempt to increase respiration and oxygenation.

There remains a need in the art for an improved ventilator.

SUMMARY OF THE INVENTION

A proportional assist ventilator system with an implantable respiration sensor is provided according to an embodiment of the invention. The implantable respiration sensor comprises a respiration sensor element capable of being implanted in a patient. The respiration sensor element generates a respiration signal related to a respiration of the patient. The implantable respiration sensor further comprises a respiration signal relay device capable of being implanted in the patient and in communication with the respiration sensor element. The respiration signal relay device is capable of communicating the respiration signal to a ventilator that is external to the patient. Using the implantable respiration sensor, a predetermined gas charge may be delivered to the patient based on the respiration signal.

A method of providing a proportional respiration assist to a patient is provided according to another embodiment of the invention. The method comprises a step of generating a respiration signal related to a respiration of the patient. The respiration signal is directly generated by a respiration sensor element implanted in the patient. The method further comprises a step of relaying the respiration signal to a ventilator. The ventilator is external to the patient. The method further comprises a step of delivering a predetermined gas charge to the patient based on the respiration signal.

A method of providing a proportional respiration assist to a patient is provided according to yet another embodiment of the invention. The method comprises a step of implanting a respiration sensor element in the patient. The respiration sensor element directly detects a respiration of the patient and generates a respiration signal related to the respiration. The method further comprises a step of implanting a respiration signal relay device in the patient. The respiration signal relay device communicates with the respiration sensor element and relays the respiration signal to a ventilator external to the patient. The ventilator is therefore capable of delivering a predetermined gas charge to the patient, with the predetermined gas charge being based on the respiration signal.

A ventilator apparatus for providing proportional assist ventilation to a patient having a respiration sensor with a wireless transmitter implanted therein is provided according to still another embodiment of the invention. The apparatus comprises a wireless receiver for receiving a respiration signal relayed by the wireless transmitter and a ventilator which delivers a predetermined gas charge to the patient based on the respiration signal.

The above and other features and advantages of the present invention will be further understood from the following description of the preferred embodiments thereof, taken in conjunction with the accompanying drawings.

DETAILED DESCRIPTION OF THE PREFERRED EMBODIMENTS

Figure 1:
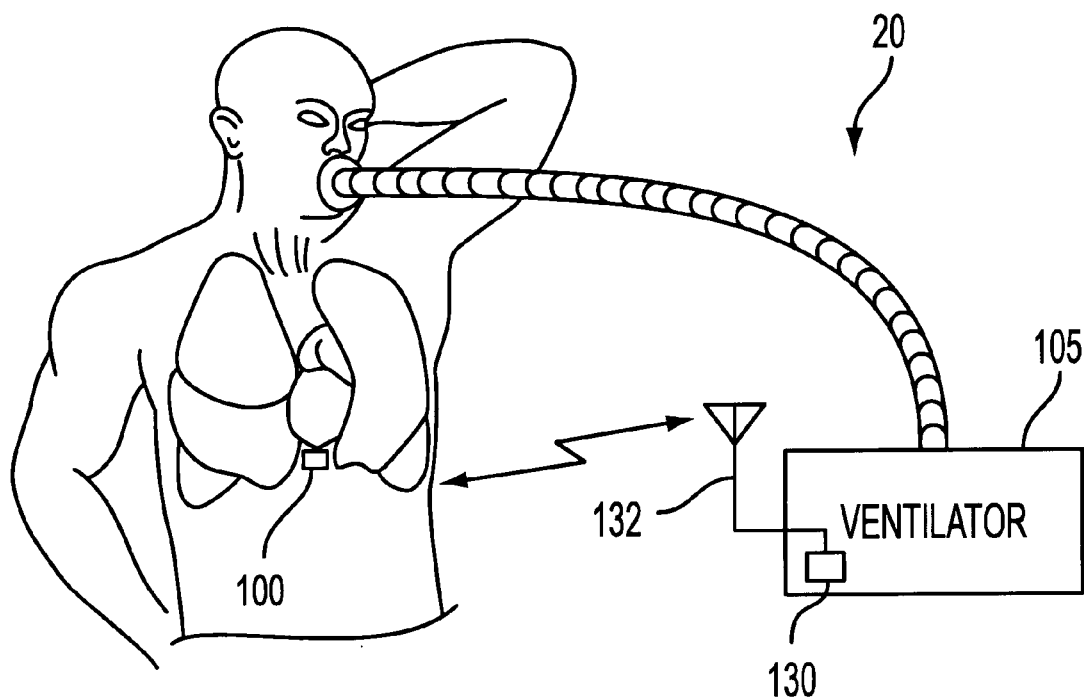
FIG. 1 shows an embodiment of a ventilator system according to the invention.

FIG. 1 shows an embodiment of a ventilator system 20 according to the invention. Ventilator system 20 includes an implantable respiration sensor 100 and a ventilator 105. The implantable respiration sensor 100 may be implanted in a patient, and generates a respiration signal that is related to the patient's respiration. The respiration signal is relayed to ventilator 105 that is external to the patient. The ventilator 105 may be any type of ventilator that is capable of regulating a gas charge output based on a respiration signal input. The ventilator 105 may use the respiration signal to regulate the ventilator output, including regulating an inhalation gas charge pressure, volume, and/or frequency. The ventilator 105 may therefore provide a gas charge that is proportional to the respiration effort of the patient, and therefore is capable of substantially proportionally assisting the respiration of the patient.

The implantable respiration sensor 100 may be implanted in the patient's thoracic cavity, such as inside the lower ribcage region, above the diaphragm muscle. The implantable respiration sensor 100 is therefore preferably located in a region where, when the diaphragm muscle contracts in order to perform inhalation, pressure exerted against the implantable respiration sensor 100 decreases.

The respiration sensor element 121 generates a varying electrical signal in response to the respiration of the patient. The respiration sensor element 121 may be any type of suitable pressure sensor, strain gauge, impedance sensor, etc. In a preferred embodiment, the respiration sensor element 121 may be a pressure sensor. The pressure sensor generates an electrical output that varies in response to a pressure exerted on the respiration sensor element 121 by the ribcage and the diaphragm muscles of the patient. Respiration is reflected in the respiration signal as a series of negative and positive peaks. The negative inhalation waveform peaks reflect the lessened pressure of the diaphragm muscle as the diaphragm muscle contracts downward in order to expand the lungs for inhalation. The positive exhalation waveform peaks reflect the increased pressure exerted by the diaphragm muscle against the ribcage as the diaphragm muscle expands upward in order to compress the lungs for exhalation. The pressure sensor embodiment of the respiration sensor element 121 therefore generates alternating positive and negative force peak signals as the diaphragm muscle expands and contracts.

In an alternative embodiment, the pressure sensor could be implanted within fibers of the diaphragm muscle and could detect pressure differences therein. In another alternative embodiment, the implantable respiration sensor 100 could be an impedance sensor implanted within fibers of the diaphragm muscle and could detect impedance differences therein. In another alternative embodiment, the implantable respiration sensor 100 could be a strain gauge affixed to a rib and measures a flex or strain imposed on the rib. In yet another embodiment, the implantable respiration sensor 100 could measure electrical nerve impulses that initiate an inhalation contraction of the diaphragm muscles. It should be understood that other sensor types other than those recited could be equally well employed.

The respiration signal may be any type of signal that conveys the current respiratory state of the patient to the ventilator 105. In a preferred embodiment, the amplitude of the signal, corresponding to the amount of muscular exertion and therefore the respiration effort, may be used to control the ventilator 105.

In addition to the respiration signal magnitude, the respiration signal width and/or frequency may give an indication that the patient is trying to achieve more airflow through longer inhalation periods or through more frequent inhalations. All of this information may be used by the ventilator 105 to regulate the gas charge delivered to the patient.

Figure 2:
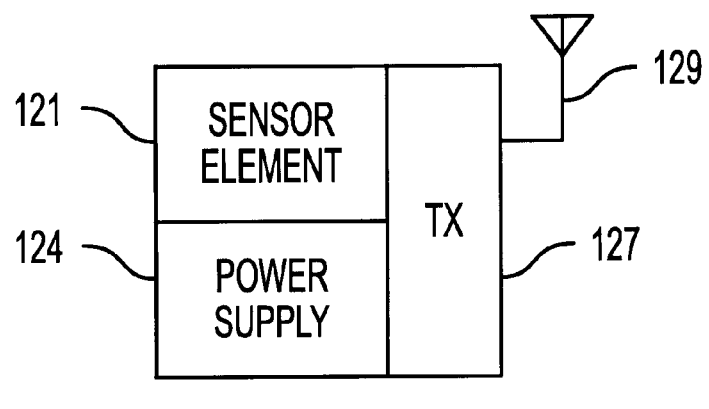
FIG. 2 shows detail of an implantable respiration sensor for use in the ventilator system of the present invention.

FIG. 2 shows detail of the implantable respiration sensor 100. The respiration signal in the embodiment shown in FIGS. 1 and 2 is relayed by a wireless link from the implantable respiration sensor 100 to the ventilator 105. The wireless link may be a radio frequency (RF) link. As shown in FIG. 2, the implantable respiration sensor 100 may include a respiration sensor element 121, a power supply 124, a wireless transmitter (TX) 127, and a transmission antenna 129. As shown in FIG. 1, ventilator 105 may include a wireless receiver 130 and a reception antenna 132.

The wireless transmitter 127 may be any type of suitable wireless transmitter, such as a radio frequency (RF) link or a magnetic or inductive link. The wireless transmitter 127 must be capable of relaying the respiration signal to the ventilator 105. The wireless transmitter 127 may use any suitable frequency band and any suitable power level capable of transmitting the respiration signal through the patient's body and relaying it to the ventilator 105. The wireless receiver 130 may be any type of suitable wireless receiver capable of receiving the respiration signal relayed by the wireless transmitter 127.

The power supply 124 may be any source of electrical power sufficient to power the respiration sensor element 121 and the transmitter 127. The power supply 124 may be, for example, a battery or a fuel cell.

Figure 3:
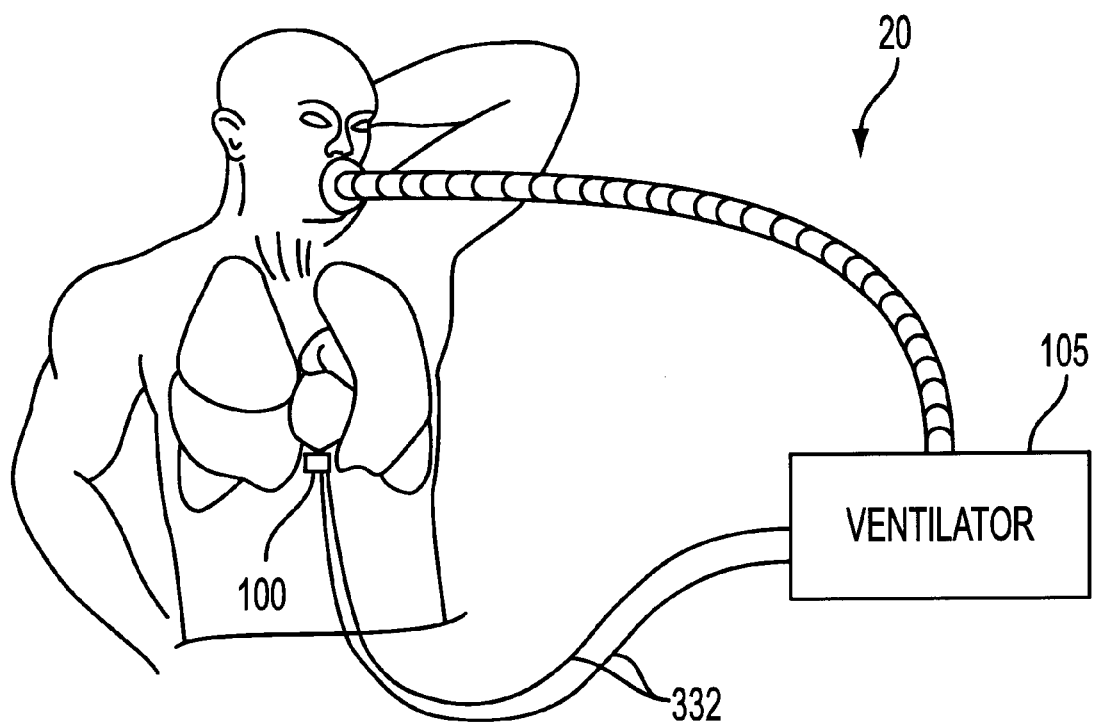
FIG. 3 shows another sensor embodiment according to the invention.

FIG. 3 shows another embodiment of a ventilator system 20 according to the invention. In this embodiment, the implantable respiration sensor 100 is connected to the ventilator 105 by a transdermal wire harness 332. The transdermal wire harness 332 emerges from the patient's body to directly relay the respiration signal to the ventilator 105. The ventilator 105 may use the respiration signal to control a gas charge supplied to the patient, as in the first embodiment.

Unlike the wireless link embodiment, the transdermal wire harness embodiment does not require an implanted power source and transmitter. Therefore, the transdermal wire harness embodiment requires only a respiration sensor element 121 implanted in the patient, along with the transdermal wire harness 332. The respiration sensor element 121 may be any of the types previously discussed. The ventilator 105 may therefore supply an electrical current to the respiration sensor element 121, which may impose the respiration signal onto the transdermal wire harness 332.

Figure 4:
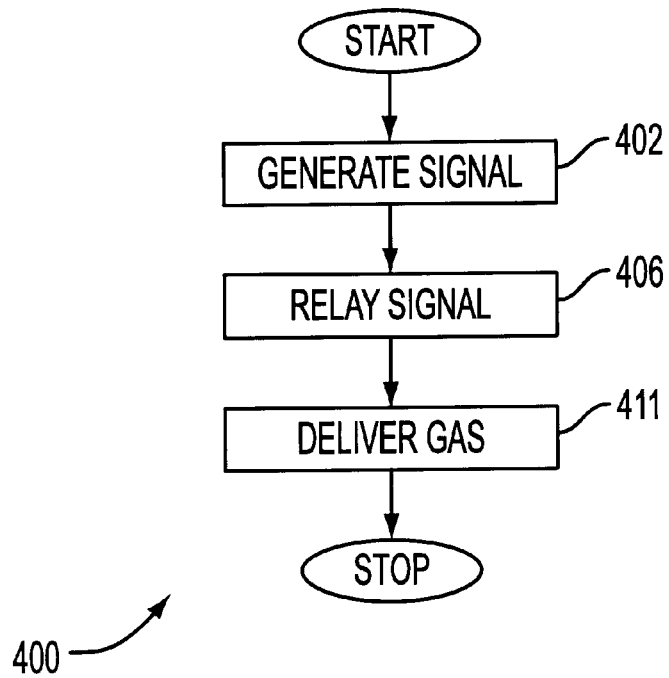
FIG. 4 is a flowchart of a method embodiment according to the invention.

FIG. 4 is a flowchart 400 of a method embodiment according to the invention. In step 402, an implantable respiration sensor 100 generates a respiration signal that is related to the respiration of a patient. The respiration signal contains information indicative of a respiration effort being expended by the patient, as previously discussed.

In step 406, the respiration signal is relayed outside of the patient's body to a ventilator 105. The relaying may be done by a wireless transmitter, such as a RF transmitter, or by a transdermal wire harness extending out of the patient's body.

In step 411, the ventilator 105 regulates a gas charge based on the respiration signal relayed from the patient's body. The respiration signal contains information about the respiration effort being expended by the patient, and therefore the ventilator 105 may regulate a gas charge to the patient based upon the patient's respiration effort. The ventilator 105 may regulate the pressure, volume, and/or frequency of the gas charge delivered to the patient in response to the respiration signal. The ventilator 105 may therefore provide a proportional assist wherein the gas charge is substantially proportional to the respiration effort of the patient.

Figure 5:
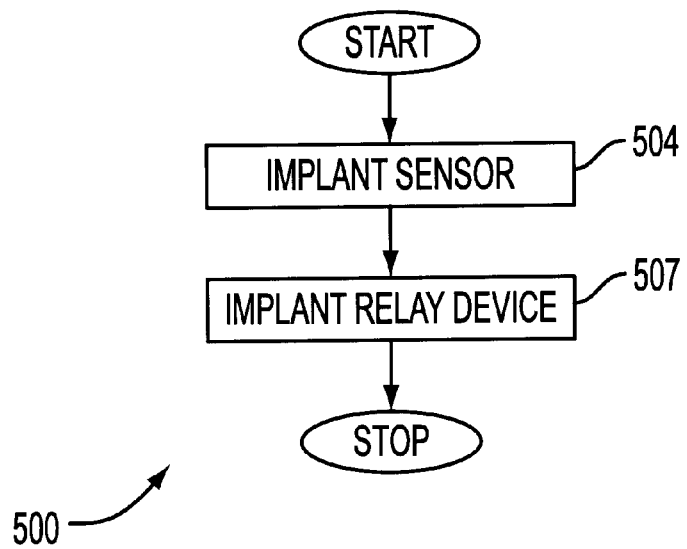
FIG. 5 is a flowchart of another method embodiment according to the invention.

FIG. 5 is a flowchart 500 of another method embodiment according to the invention. In step 504, an implantable respiration sensor 100 is implanted into the patient's body. The implantable respiration sensor 100, when implanted, is capable of directly detecting the respiration of the patient. More importantly, the implantable respiration sensor 100 is capable of detecting the respiration effort of the patient. The implantable respiration sensor 100 may be implanted in a thoracic cavity of the patient, such as between the ribcage and the diaphragm muscle.

In step 507, a relay device is implanted into the patient's body. The relay device communicates with the implantable respiration sensor 100 and operates to relay the respiration signal to the ventilator 105. The relay device may be a wireless link, such as a RF link, for example, or may be a transdermal wire harness. The respiration signal relayed to the ventilator 105 may be used by the ventilator to regulate a gas charge. By generating a respiration signal and relaying the respiration signal to the ventilator 105, the ventilator 105 is able to directly determine the characteristics of the gas supply charge to be supplied to the patient. In addition, the respiration signal is provided to the ventilator 105 with minimal delay, allowing the ventilator 105 to react quickly to changes in the patient's respiration.

As an additional advantageous feature of the invention, the respiration signal may additionally be provided to other medical equipment, such as cardiac monitoring equipment, for example. In addition, the respiration signal may be recorded for a patient history and studied and may be used to generate an alert signal based upon any breathing abnormality of the patient.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A ventilator system for providing a gas to a patient, comprising:
    a ventilator;
    a respiration sensor element capable of being implanted in a patient, with said respiration sensor element generating a respiration signal related to a respiration of said patient; and
    a respiration signal relay device capable of being implanted in said patient and in communication with said respiration sensor element, with said respiration signal relay device being capable of communicating said respiration signal to said ventilator;
    wherein a predetermined gas charge may be delivered to said patient by said ventilator based on said respiration signal.

2. The ventilator system of claim 1, wherein said respiration sensor element is implanted in a thoracic cavity of said patient.

3. The ventilator system of claim 1, wherein said respiration signal is related to a respiration effort of said patient.

4. The ventilator system of claim 1, wherein an amplitude of said respiration signal is related to a respiration effort of said patient.

5. The ventilator system of claim 1, wherein said respiration sensor element is a pressure sensor.

6. The ventilator system of claim 1, wherein said respiration sensor element is a strain gauge.

7. The ventilator system of claim 1, wherein said respiration sensor element is an impedance sensor.

8. The ventilator system of claim 1, wherein said respiration signal relay device is a radio frequency transmitter connected to said respiration sensor element and capable of transmitting a radio frequency respiration signal to said ventilator.

9. The ventilator system of claim 1, wherein said respiration signal relay device is a transdermal wire harness connected to said respiration sensor element and capable of transmitting said respiration signal to said ventilator.

10. A method of providing a proportional respiration assist to a patient, comprising the steps of:
    generating a respiration signal related to a respiration of said patient, said respiration signal being directly generated by a respiration sensor element implanted in said patient;
    relaying said respiration signal to a ventilator, said ventilator being external to said patient; and
    delivering a predetermined gas charge to said patient based on said respiration signal.

11. The method of claim 10, wherein said respiration sensor element is implanted in a thoracic cavity of said patient.

12. The method of claim 10, wherein said respiration signal is related to a respiration effort of said patient.

13. The method of claim 10, wherein an amplitude of said respiration signal is related to a respiration effort of said patient.

14. The method of claim 10, wherein said ventilator regulates a predetermined gas charge pressure based on said respiration signal.

15. The method of claim 10, wherein said ventilator regulates a predetermined gas charge volume based on said respiration signal.

16. The method of claim 10, wherein said ventilator regulates a predetermined gas charge duration based on said respiration signal.

17. The method of claim 10, wherein said ventilator regulates a predetermined gas charge frequency based on said respiration signal.

18. A method of providing a proportional respiration assist to a patient, comprising the steps of:
    implanting a respiration sensor element in said patient, said respiration sensor element directly detecting a respiration of said patient and generating a respiration signal related to said respiration; and
    implanting a respiration signal relay device in said patient, with said respiration signal relay device communicating with said respiration sensor element and relaying said respiration signal to a ventilator external to said patient; and
    delivering a predetermined gas charge to said patient from said ventilator based on said respiration signal.

19. The method of claim 18, wherein said respiration sensor element is implanted in a thoracic cavity of said patient.

20. The method of claim 18, wherein said respiration signal is related to a respiration effort of said patient.

21. The method of claim 18, wherein an amplitude of said respiration signal is related to a respiration effort of said patient.

22. The method of claim 18, wherein said ventilator regulates a predetermined gas charge pressure based on said respiration signal.

23. The method of claim 18, wherein said ventilator regulates a predetermined gas charge volume based on said respiration signal.

24. The method of claim 18, wherein said ventilator regulates a predetermined gas charge duration based on said respiration signal.

25. The method of claim 18, wherein said ventilator regulates a predetermined gas charge frequency based on said respiration signal.

26. A ventilator apparatus for providing proportional assist ventilation to a patient having a respiration sensor with a wireless transmitter implanted therein, said apparatus comprising
    a wireless receiver capable of receiving a respiration signal relayed by the wireless transmitter; and
    a ventilator capable of delivering a predetermined gas charge to the patient based on the respiration signal.

27. The ventilator apparatus of claim 26, wherein said wireless receiver is disposed within said ventilator.

* * * * *